United States Patent
Ellis

(10) Patent No.: US 7,174,254 B2
(45) Date of Patent: Feb. 6, 2007

(54) MUD GAS ISOTOPE LOGGING INTERPRETATIVE PROCESS UTILIZING MIXING LINES IN OIL AND GAS DRILLING OPERATIONS

(76) Inventor: Leroy Ellis, 206 Hyde Park Dr., Richardson, TX (US) 75080

( * ) Notice: Subject to any disclaimer, the term of this patent is extended or adjusted under 35 U.S.C. 154(b) by 0 days.

(21) Appl. No.: 10/952,136

(22) Filed: Sep. 28, 2004

(65) Prior Publication Data

US 2005/0256647 A1    Nov. 17, 2005

Related U.S. Application Data

(63) Continuation-in-part of application No. 10/845,743, filed on May 13, 2004, now Pat. No. 7,124,030.

(51) Int. Cl.
*G01V 9/00* (2006.01)
(52) U.S. Cl. .............................. 702/9; 702/13
(58) Field of Classification Search ................ 702/6, 702/8, 9, 13
See application file for complete search history.

(56) References Cited

U.S. PATENT DOCUMENTS 3,033,287 A * 5/1962 Bond ................. 166/250.16
5,388,456 A * 2/1995 Kettel ................. 73/152.02

* cited by examiner

*Primary Examiner*—Donald McElheny, Jr.
(74) *Attorney, Agent, or Firm*—Michael Diaz

(57) ABSTRACT

The present invention is a method of interpreting sampled mud gas compositional and isotopic data from a target area in a drilling operation. The compositional and isotopic data is plotted on a chart. The chart preferably illustrates methane compositional data together with isotopic composition, such as $\delta^{13}C_1$. From this chart, mixing lines are determined. The mixing lines are determined by finding data points plotted on the chart which approximate a straight line or other trend. The mixing lines are then analyzed to determine reservoir isotopic signature, hydrocarbon communication and any interference to this communication within the target area.

21 Claims, 12 Drawing Sheets

| Depth (ft) | Total Gas (Rig. units) | Total HC (Lab. vol%) | %C1 | %C2 | %C3 | %iC4 | %nC4 | %iC5 | %nC5 | %C6+ | Dryness %C1/Cn | Wetness %C2/Cn | $\delta^{13}C_1$ | $\delta^{13}C_2$ | $\delta^{13}C_3$ |
|---|---|---|---|---|---|---|---|---|---|---|---|---|---|---|---|
| 2150 |  | 0.22 | 0.21 |  |  |  |  |  |  |  | 97.54 |  | -58.6 |  |  |
| 2300 | 19 | 0.26 | 0.26 |  |  |  |  |  |  |  | 100 |  | -52.0 |  |  |
| 2450 |  | 0.99 | 0.97 | 0.014 |  |  |  |  |  |  | 98.26 | 1.42 | -45.1 |  |  |
| 2600 | 65 | 1.10 | 1.08 | 0.012 | 0.001 |  | 0.001 | 0.001 | 0.002 |  | 98.19 | 1.09 | -44.1 |  |  |
| 2750 |  | 0.89 | 0.87 | 0.007 |  |  |  |  |  |  | 98.13 | 0.82 | -46.6 |  |  |
| 2900 |  | 0.01 | 0.01 |  |  |  |  |  |  |  | 100 |  |  |  |  |
| 3050 | 136 | 1.15 | 1.13 | 0.011 | 0.002 | 0.001 | 0.001 | 0.001 | 0.001 |  | 98.42 | 0.96 | -48.4 |  |  |
| 3200 |  | 2.19 | 2.16 | 0.018 | 0.006 | 0.002 |  |  |  |  | 98.79 | 0.82 | -49.2 |  |  |
| 3350 |  | 0.79 | 0.79 | 0.003 | 0.004 | 0.001 |  |  |  |  | 99.61 | 0.39 | -49.0 |  |  |
| 3500 | 54 | 0.65 | 0.65 | 0.003 |  |  |  |  |  |  | 99.49 | 0.51 | -48.2 |  |  |
| 3650 |  | 0.83 | 0.82 | 0.008 | 0.004 |  |  |  |  |  | 98.62 | 1.00 | -47.3 |  |  |
| 3800 |  | 0.36 | 0.35 | 0.006 | 0.004 |  |  |  |  |  | 96.77 | 1.58 | -46.6 |  |  |
| 3950 |  | 0.82 | 0.78 | 0.024 | 0.002 | 0.002 | 0.001 | 0.001 | 0.001 |  | 94.58 | 2.91 | -44.7 |  |  |
| 4100 |  | 0.91 | 0.85 | 0.031 | 0.003 | 0.003 | 0.002 | 0.001 | 0.001 |  | 93.51 | 3.41 | -44.4 |  |  |
| 4250 |  | 0.97 | 0.87 | 0.051 | 0.013 | 0.006 | 0.005 | 0.002 | 0.002 |  | 90.00 | 5.28 | -41.6 |  |  |
| 4293 | 550 | 7.73 | 6.71 | 0.470 | 0.280 | 0.071 | 0.061 | 0.061 | 0.074 | 0.001 | 86.84 | 6.03 | -42.0 |  |  |
| 4311 | 760 | 9.81 | 8.59 | 0.600 | 0.340 | 0.081 | 0.063 | 0.063 | 0.070 | 0.001 | 87.59 | 6.42 | -42.0 |  |  |
| 4326 | 120 | 1.30 | 1.16 | 0.071 | 0.038 | 0.010 | 0.008 | 0.008 | 0.010 | 0.002 | 88.00 | 5.44 | -42.2 |  |  |
| 4360 | 200 | 2.44 | 2.14 | 0.140 | 0.081 | 0.019 | 0.018 | 0.018 | 0.021 | 0.005 | 87.81 | 5.74 | -42.1 |  |  |
| 4423 | 125 | 1.42 | 1.24 | 0.086 | 0.047 | 0.011 | 0.010 | 0.010 | 0.012 | 0.012 | 87.57 | 5.07 | -41.9 |  |  |
| 4514 | 700 | 13.41 | 12.6 | 0.430 | 0.220 | 0.037 | 0.025 | 0.025 | 0.030 | 0.030 | 94.28 | 3.21 | -42.5 | -34.7 | -33.1 |
| 4565 | 390 | 4.57 | 3.97 | 0.280 | 0.100 | 0.037 | 0.029 | 0.029 | 0.034 | 0.034 | 86.89 | 6.13 | -41.6 |  |  |
| 4576 | 850 | 11.16 | 9.91 | 0.610 | 0.400 | 0.077 | 0.053 | 0.053 | 0.059 | 0.059 | 88.78 | 5.46 | -42.9 | -33.7 | -32.7 |
| 4600 | 220 | 2.38 | 2.11 | 0.140 | 0.080 | 0.015 | 0.011 | 0.011 | 0.014 | 0.014 | 88.62 | 5.88 | -42.4 |  |  |
| 4650 |  | 1.58 | 1.40 | 0.091 | 0.059 | 0.019 | 0.009 | 0.009 | 0.012 | 0.012 | 88.43 | 5.75 | -42.6 | -34.0 | -32.9 |
| 4700 |  | 2.61 | 2.33 | 0.140 | 0.078 | 0.015 | 0.014 | 0.014 | 0.018 | 0.018 | 89.34 | 5.37 | -42.8 |  |  |
| 4714 | 1700 | 45.61 | 43.2 | 1.530 | 0.350 | 0.100 | 0.046 | 0.046 | 0.041 | 0.041 | 94.71 | 3.35 | -43.9 | -33.5 | -32.5 |
| 4900 | 140 | 1.93 | 1.78 | 0.089 | 0.033 | 0.008 | 0.006 | 0.006 | 0.007 | 0.007 | 92.32 | 4.62 | -43.8 |  |  |
| 5050 |  | 0.30 | 0.27 | 0.014 | 0.005 | 0.002 | 0.003 | 0.003 | 0.004 | 0.004 | 89.79 | 4.66 | -44.2 |  |  |

| | | | | | | | | | | | |
|---|---|---|---|---|---|---|---|---|---|---|---|
| 5350 | 80 | 1.19 | 1.15 | 0.024 | 0.007 | | | | | 96.73 | 2.02 | -46.9 |
| 5500 | 80 | 1.21 | 1.17 | 0.025 | 0.008 | | | | | 96.60 | 2.06 | -48.0 |
| 5650 | 60 | 1.38 | 1.33 | 0.033 | 0.012 | | | | | 96.73 | 2.40 | -48.1 |
| 5800 | | 0.98 | 0.94 | 0.030 | 0.013 | 0.001 | | | | 95.54 | 3.05 | -48.4 |
| 5950 | 92 | 0.95 | 0.89 | 0.037 | 0.017 | 0.001 | 0.002 | 0.002 | 0.003 | 94.06 | 3.91 | -48.5 |
| 6100 | 42 | 1.44 | 1.32 | 0.074 | 0.039 | 0.002 | 0.002 | 0.002 | 0.003 | 91.53 | 5.13 | -48.4 |
| 6250 | | 0.80 | 0.73 | 0.039 | 0.023 | 0.001 | 0.002 | 0.002 | 0.001 | 91.11 | 4.87 | -47.6 |
| 6400 | | 1.10 | 0.96 | 0.074 | 0.048 | 0.001 | 0.005 | 0.005 | 0.001 | 87.02 | 6.71 | -48.8 |
| 6550 | | 0.72 | 0.62 | 0.047 | 0.033 | 0.004 | 0.004 | 0.005 | 0.002 | 86.65 | 6.57 | -48.4 |
| 6700 | | 1.16 | 1.02 | 0.078 | 0.047 | 0.003 | 0.006 | 0.004 | 0.005 | 87.83 | 6.72 | -48.9 |
| 6850 | | 0.83 | 0.72 | 0.060 | 0.037 | 0.004 | 0.004 | 0.003 | 0.004 | 86.67 | 7.22 | -48.7 |

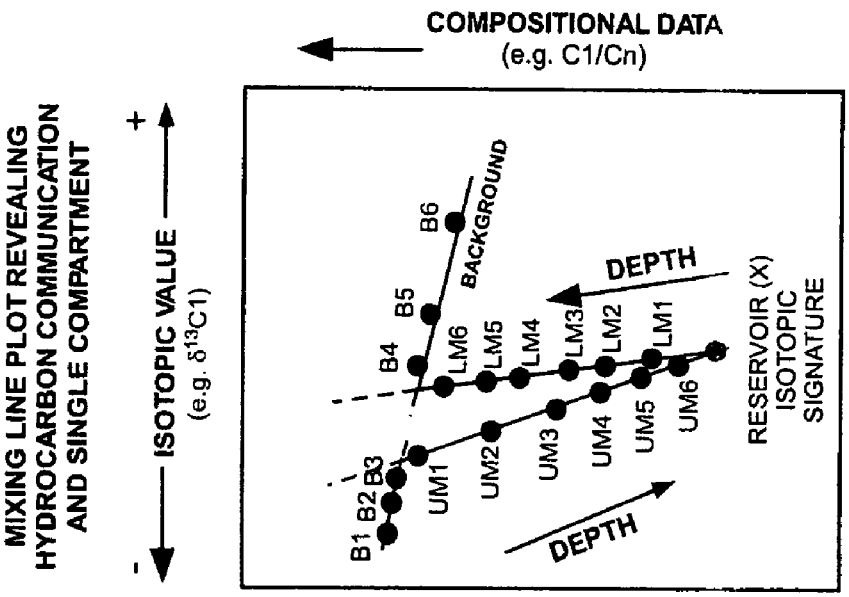
FIG 5C
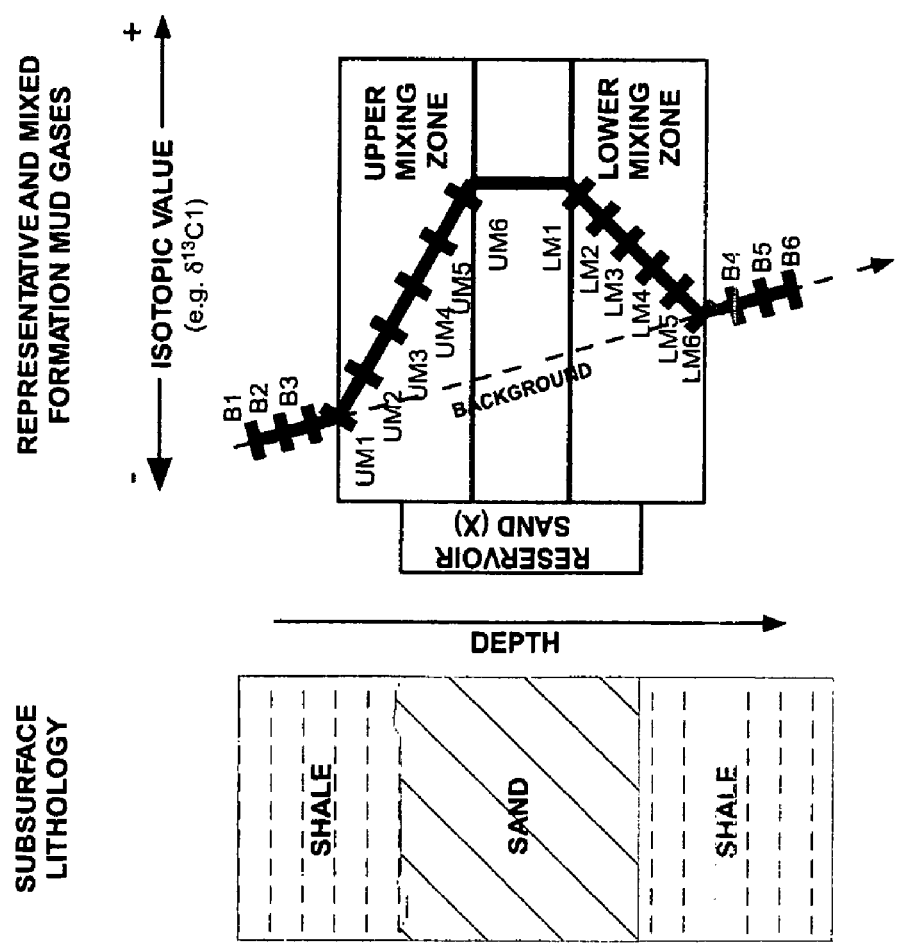
FIG 5B
FIG 5A

MUD GAS ISOTOPE LOGGING INTERPRETATIVE PROCESS UTILIZING MIXING LINES IN OIL AND GAS DRILLING OPERATIONS

RELATED APPLICATIONS

This application is a continuation-in-part application of U.S. patent application Ser. No. 10/845,743 now U.S. Pat. No. 7,124,030 entitled "MUD GAS ISOTOPE LOGGING INTERPRETIVE METHOD IN OIL AND GAS DRILLING OPERATIONS" filed on May 13, 2004 under the name of Leroy Ellis and is hereby incorporated by reference.

BACKGROUND OF THE INVENTION

1. Field of the Invention

This invention relates to isotopic analysis associated with oil and gas drilling operations. Specifically, the present invention relates to an interpretive method utilizing newly developed mixing lines from derived mud gas isotope logging data to assess reservoir compartmentalization and hydrocarbon communication concomitant with identification of lithological seals, baffles and barriers.

2. Description of the Related Art

Laboratory analysis of gas samples obtained during a drilling operation may be employed to determine geochemical information associated with strikes of oil or gas deposits. The laboratory analysis may include the acquisition of compositional and isotopic data of sampled subsurface gases. This data is applied to traditional geochemical plots and templates. The interpretation of this data is used to provide geochemical information on the oil and gas provenance, how thermally mature the hydrocarbons are, whether subsurface post-generation effects were encountered during migration of the gaseous hydrocarbons from the source rock to a reservoir, and any problems or effects the hydrocarbons in the reservoir subsequently experienced.

Existing well sampling techniques use physical gas samples for compositional and isotopic laboratory analyses, obtained via wellheads, separators, down-hole logging tools (e.g., modular dynamic tester/repeat formation tester, etc.), canned cuttings, and/or sampled gases entrained in the mud system during drilling.

As discussed in co-pending U.S. patent application Ser. No. 10/845,743 ('743), there are several problems and issues not adequately addressed using standard mud gas chromatographic compositional analyses and interpretations. None of the existing techniques effectively detail or correlate geological information such as lithological hydrocarbon seals, baffles and barriers, good communication compartments, or gas diffusion and/or leakage into their interpretation. Compositional data can result in false positives and negatives where changes in operational conditions related to drilling variables such as increased rate of penetration or mud weight increases occur. '743 provides a far more advanced method which applies new interpretative techniques involving mud gas chromatographic compositional and isotopic analyses together with detailed drilling, geological and engineering information integration.

Within the improved interpretative techniques disclosed in '743 is the newly developed use of hydrocarbon mixing lines to determine or suggest good hydrocarbon communication compartments and zones. Mixing lines are identified on plots where hydrocarbon gas compositional and isotopic data are plotted. The mixing lines are defined by data points falling along a plotted trend line, suggesting a depth section in the well that is in good gas communication, and therefore representative of a compartment. Breaks in any of the mixing lines identify approximate depth locations at which lithological seals, baffles or other barriers to hydrocarbon communication may in fact be present. The depth range of each line may be considered to reflect or suggest an interval of good hydrocarbon communication. Furthermore, a number of seals, baffles and barriers are suggested defining these intervals, supporting the interpretation that these intervals may be likely to show localized hydrocarbon communication zones concomitant with potentially serious compartmentalization issues.

Thus, it would be a distinct advantage to have an interpretive method of analysis of mud gas samples utilizing chromatographic compositional and isotopic analysis together with an integrated geochemical, geological, and engineering interpretation applied to the data based on the use of these mixing lines. It is an object of the present invention to provide such an interpretative method specific to mud gas isotope logging.

SUMMARY OF THE INVENTION

In one aspect, the present invention is a method of interpreting sampled mud gas compositional and isotopic data in a drilling operation of a target area. The method begins by obtaining a plurality of mud gas samples from a target area using continuous flow systems or use of gas sampling devices. Next, the plurality of mud gas samples is analyzed to obtain isotopic data from the samples. The isotopic data are then plotted on the chart. A trend is then determined upon the chart from a plurality of data points. An interpretation is then derived from the trend indicative of hydrocarbon communication, seals, baffles or other barriers to hydrocarbon communication.

In another aspect, the present invention is a method of interpreting sampled mud gas compositional and isotopic data from a target area and plotted on a chart. Mixing lines are determined from the chart from at least three data points approximating a straight or other trend line on the chart. Next, the mixing lines are analyzed to determine reservoir hydrocarbon isotopic signature, hydrocarbon communication, seals, baffles or other barriers to hydrocarbon communication within the target area.

In still another aspect, the present invention is a method of interpreting sampled mud gas compositional and isotopic data from a target area in a drilling operation. In this method, the compositional and isotopic data is plotted upon a chart. The chart illustrates a percentage hydrocarbon gas component versus associated isotopic composition for the sampled mud gas data. Next, mixing lines are determined from the chart by finding at least three data points which approximate a straight or other trend line on the chart. Then, the mixing lines are analyzed to determine reservoir hydrocarbon isotopic signature, hydrocarbon communication, seals, baffles or other barriers to hydrocarbon communication within the target area.

BRIEF DESCRIPTION OF THE DRAWINGS

FIG. 2 is an exemplary table illustrating tabulated data of a typical mud gas composition and gas isotope sampling data for a drilling well;

FIGS. 5A–5C illustrate the principles of the mixing processes in mud gas samples;

DESCRIPTION OF THE INVENTION

Figure 1:
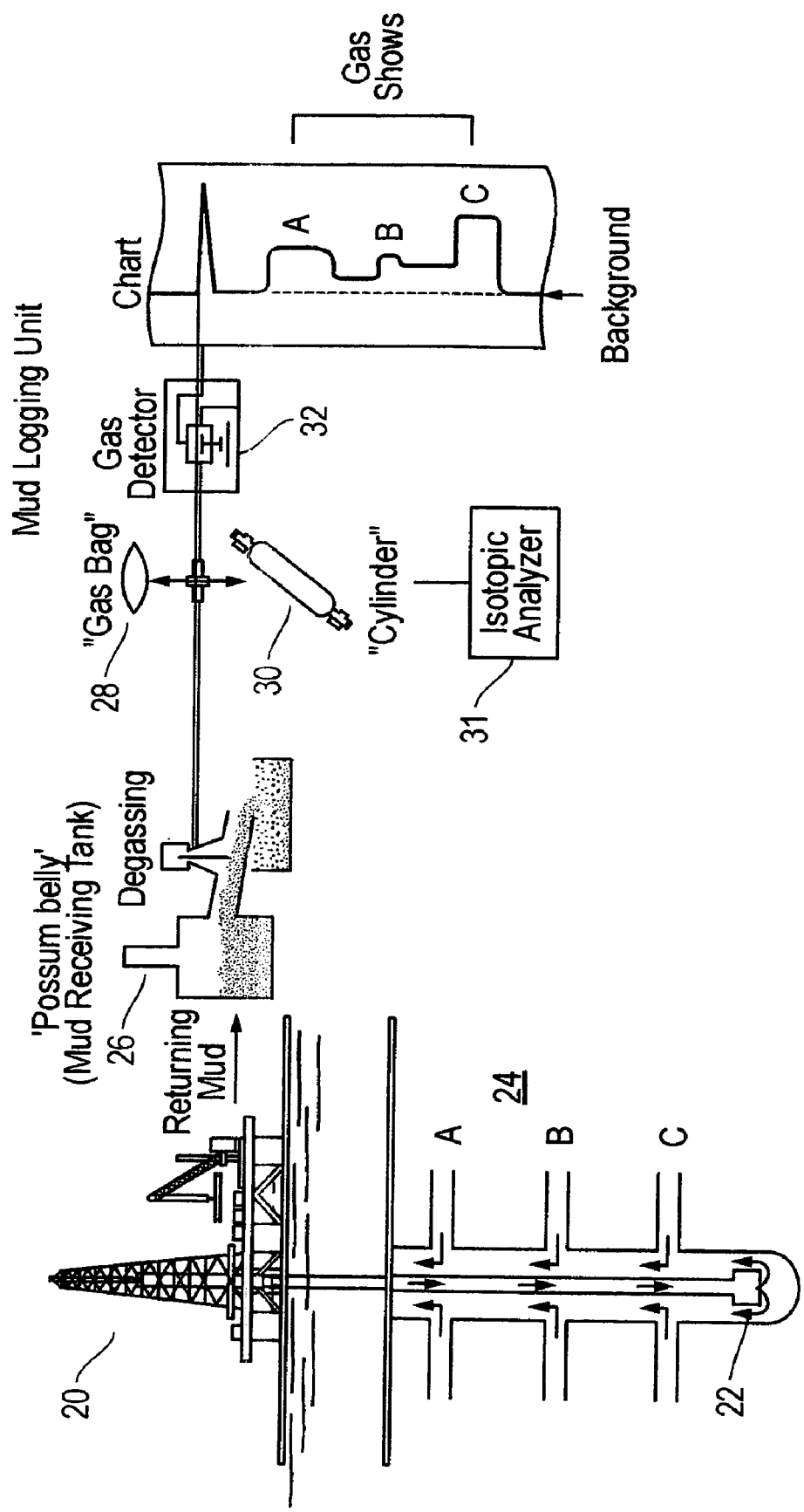
FIG. 1 is a block diagram illustrating principles of mud circulation during drilling operations and sampling of mud gases in the preferred embodiment of the present invention.

The present invention is a novel interpretive method of mud gas isotope logging utilizing mixing lines to determine reservoir hydrocarbon isotopic signature, good hydrocarbon communication, seals, baffles or other barriers to hydrocarbon communication in oil and gas drilling prospects. FIG. 1 is a block diagram illustrating principles of mud circulation during drilling operations and sampling of mud gases in the preferred embodiment of the present invention. A well 20 having a drill 22 drills down into the ground 24. Levels A, B, and C provide exemplary gas shows related to subsurface reservoirs. Mud is circulated around the drill 22 to provide lubrication for the drill and removing debris (cuttings) as it drills. The mud is circulated to the surface. The returning mud is collected on the surface within a mud receiving tank 26, also known as a possum belly. The gas is mechanically or otherwise degassed/exsolved form the mud and may be collected within a gas sampling device 28, a cylinder 30, or delivered to a mobile/onsite/in-situ isotopic analyzer 31. Typically, at a remote laboratory, mud logging unit, or an isotopic analyzer 31, a gas detector 32 (such as a gas chromatograph or mass spectrometer) is also utilized to measure compositional ratios of different hydrocarbon species.

In the preferred embodiment of the present invention, for a new drilling well, the samples are taken at regular depths (e.g., every 150–500 feet), throughout the entire well in order to establish a background trend, and more frequently in oil and gas show intervals. Once a background is established in a field, the spacing may be relaxed to a 500-foot or greater interval on later wells as more experience and knowledge is gained in the area. Additionally, gas samples collected in gas sampling devices typically see more restricted gas diffusion in the mud stream on the way to the surface as opposed to canned-cuttings that may smear, distribute or be collected over a wide composite depth interval in the mud system due to inherent density and fractal characteristic differences. Therefore, the sample depth recorded for the gas sampling devices is considered to more closely approximate the actual depth, whereas canned cuttings by nature may not accurately indicate the actual depth as rock density and fractal variables come into play In the mud system.

FIG. 2 is an exemplary table illustrating tabulated data of a typical mud gas composition and gas isotope sampling data for a drilling well. As discussed above, samples are taken at regular intervals through the well. The gas compositional data and carbon isotopic data may be arranged in any fashion. As illustrated in FIG. 2, matching rows are characterized by depth of the samples.

Figure 3:
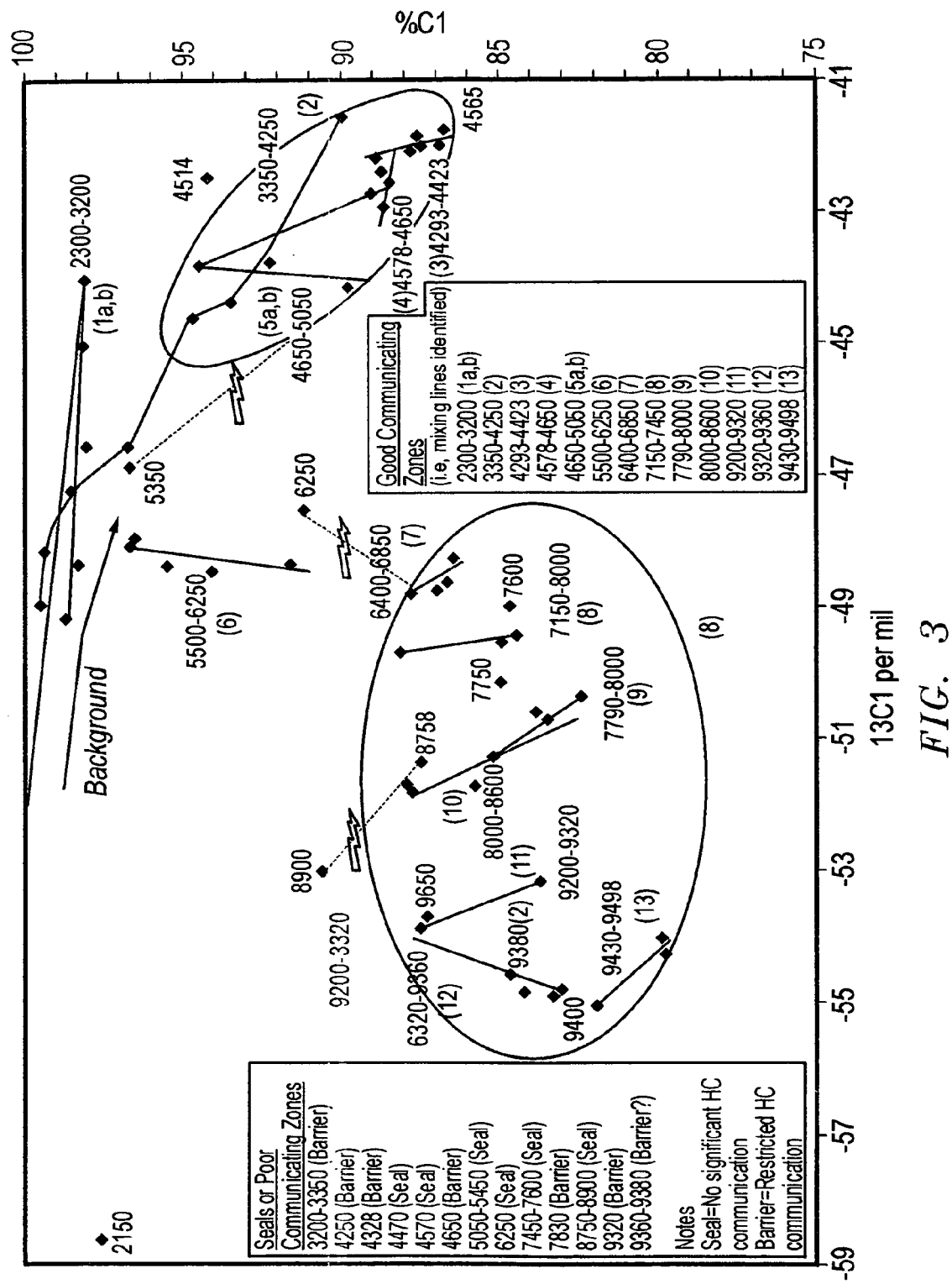
FIG. 3 is a chart illustrating a percentage C1 versus isotopic data chart in the preferred embodiment of the present invention.

FIG. 3 is a chart illustrating a percentage C1 versus corresponding and related isotopic data (e.g., $\delta^{13}C$, $^2H$) chart in the preferred embodiment of the present invention. Percentage C1 may be illustrated on the one axis (e.g., Y-axis) and isotopic data displayed on the other axis (e.g., x-axis). Straight lines (which usually are defined by at least three sequential depth data points) or other identified trends within the data are then identified and referred to as "mixing lines." These mixing lines equate to subsurface zones (compartments) in hydrocarbon gas communication. The points where the mixing lines start and end typically reveal "breaks" which may equate to lithological hydrocarbon communication seals, baffles or barriers. Baffles and barriers typically occur where a simple break in a mixing line occurs. Seals typically occur where the break is significant and the next depth data point deviates substantially. Either the next mixing line reverses direction or the next data point is far removed from the previous depth data point or mixing line. If the next (adjacent) mixing line reverses direction from one mixing line to another mixing line, this may represent one compartment where the point of reversal between the mixing lines may be representative of the actual reservoir hydrocarbon isotopic signature. If the next (adjacent) mixing line is substantially deviated, then a lithological seal, baffle or barrier may be indicated. FIG. 3 may include depth range labeling for any mixing line. Additionally, straight line-of-best-fit may also be drawn for data approximating a mixing line. Data groups that are tightly clustered are similarly interpreted to indicate good communication zones, analogous to mixing lines.

Figure 4:
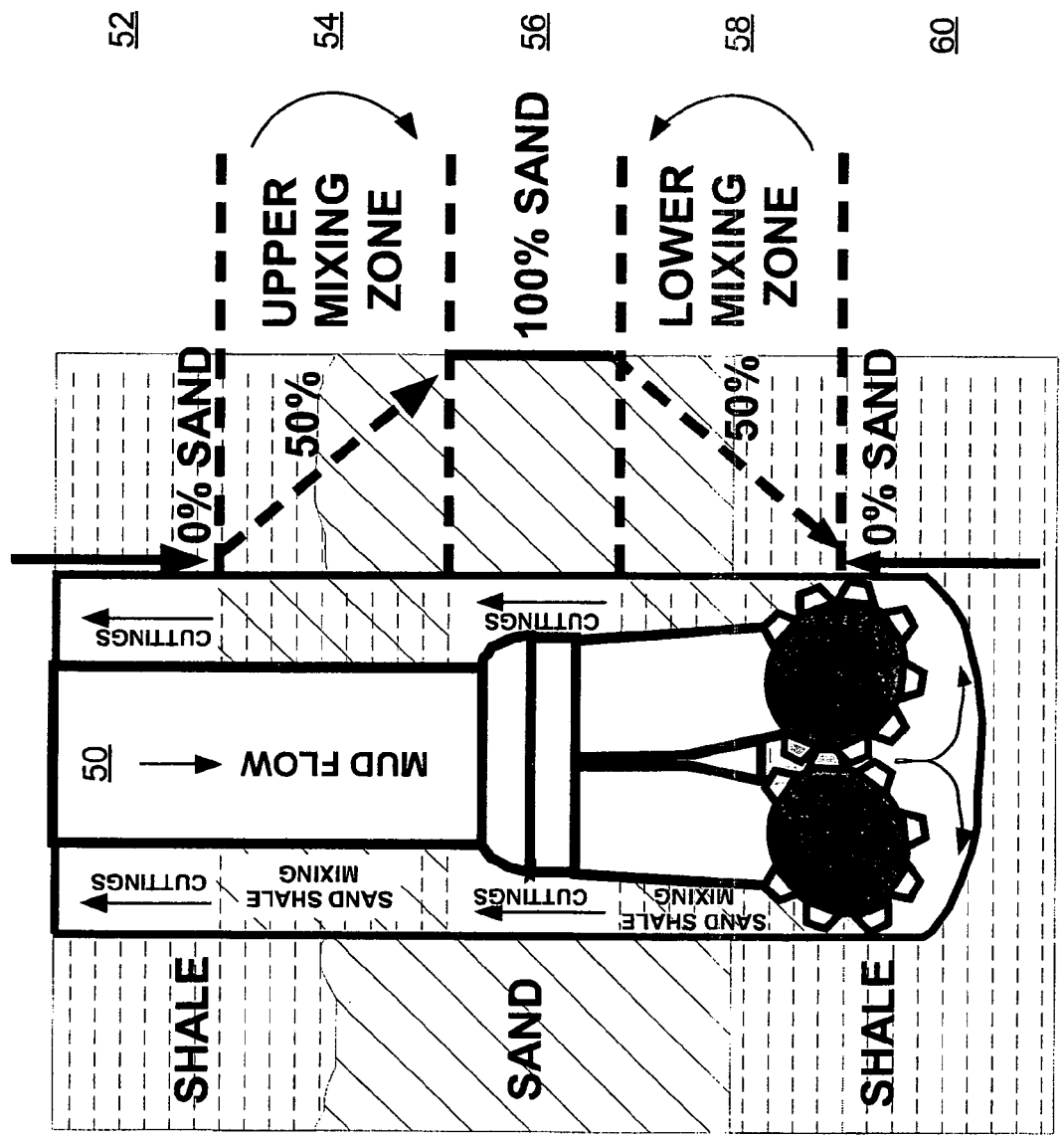
FIG. 4 is an example lithology illustrating the principles of lithology mixing of drilling cuttings in mud-stream at sand/shale boundaries.

FIGS. 4–11, discussed below, provide an explanation and illustrate examples of the principles involves in interpreting the data. FIG. 4 is a lithology illustrating the mixing of cuttings in a mud stream at sand/shale boundaries. Mud flows from a drill bore 50 (associated with drill 22) and moves upward as illustrated. As shown in FIG. 4, an upper shale area 52 overlays an upper mixing zone 54, a sand region 56, a lower mixing zone 58, and a lower shale area 60. The shale cuttings may mix with the sand region from above due to the higher density of the shale cuttings. The shale cuttings from the lower shale area may also invade the sand region due to higher frictional and fractal characteristics.

Figures 6A, 6B, 6C:
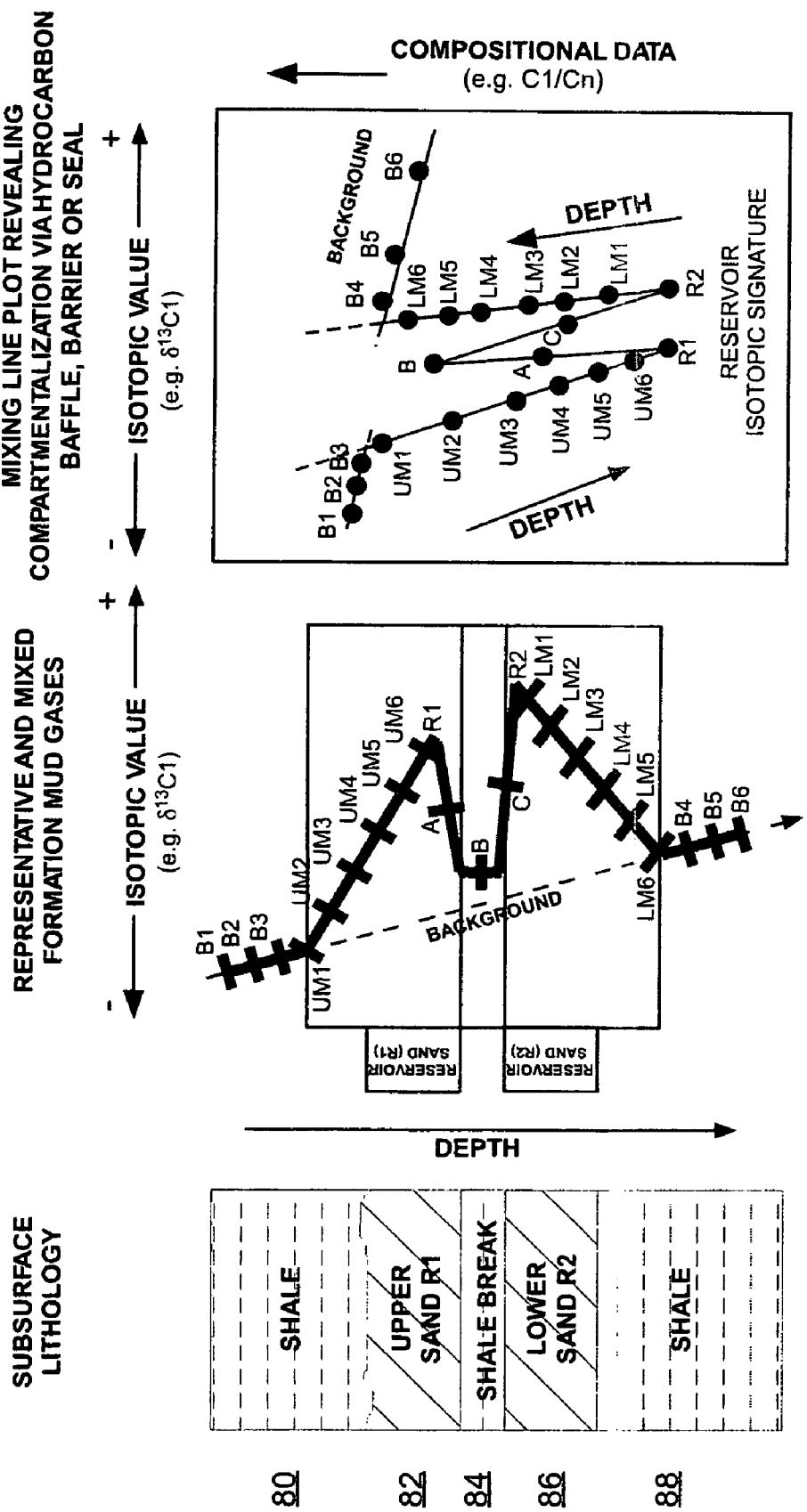
FIGS. 6A–6C illustrates the prediction of reservoir compartments and discontinuous reservoirs separated by seals, baffles or barriers via a thin shale lithology example.

FIGS. 5A–5C illustrate the principles of related gas mixing processes entrained in drilling muds. FIG. 5A illustrates the lithology by showing the upper shale area 52, the sand region 56, and the lower shale area 60. The shales from the upper shale area 52 tend to cave. Specifically, shales may sink into the sand region due to lower buoyancy and higher density (more solids per volume) characteristics. Shale in the lower shale area 60 may upwell into the sand region due to higher frictional and/or fractal characteristics (more drag upwards; more particles/volume mud). FIG. 5B illustrates a chart showing depth versus $\delta^{13}C_1$. FIG. 5C is a gas mixing plot showing C1/Cn versus $\delta^{13}C_1$ or other isotopic data. The intersection of the top and bottom of the mixing line determines reservoir composition of one continuous reservoir where the point of reversal between the mixing lines may be representative of the actual reservoir hydrocarbon isotopic signature. The mixing of lithologies results in the mixing of gases. Mixing plots allow differentiation between hanging and footwall mixing FIGS. 6A–6C illustrates the prediction of reservoir compartments and discontinuous reservoirs separated by a thin shale, other lithology or geological phenomena. FIG. 6A illustrates the lithology showing an upper shale region 80, a sand region 82, a shale break 84, a sand region 86, and a lower shale region 88. Within the sand region 82 is a reservoir R1. Within the sand region 86 is a second reservoir R2. In a similar manner as FIG. 5B, FIG. 6B illustrates the processes of gas mixing and expected isotopic mixing trends in a reservoir separated by a thin shale. FIG. 6C illustrates a gas mixing plot showing C1/Cn versus $\delta^{13}C_1$.

Figure 7:
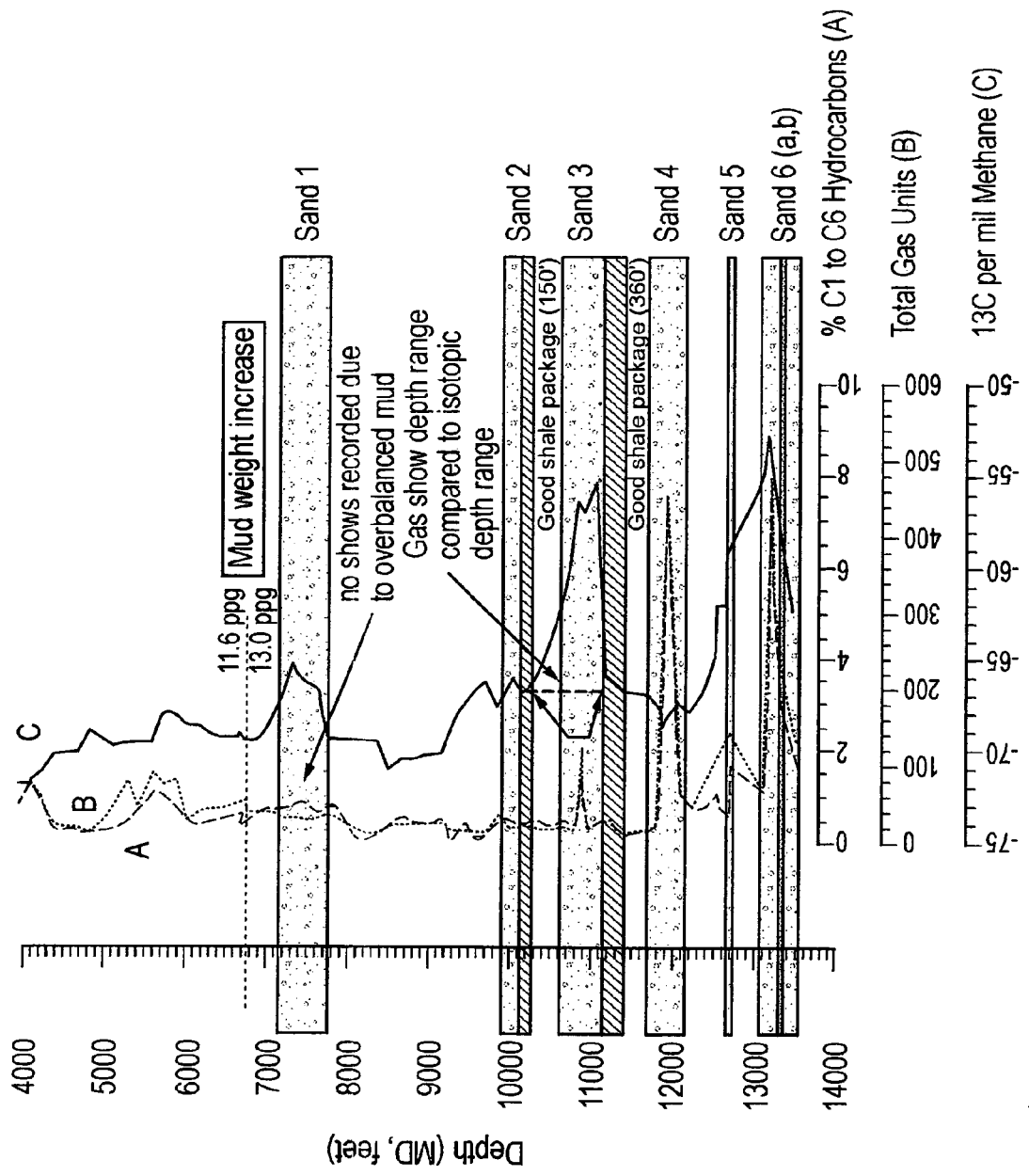
FIG. 7 illustrates an example drilling well log formed by a percentage summed C1 to C6 hydrocarbons, gas units, and 13C methane isotopic data at various depths.
Figure 8:
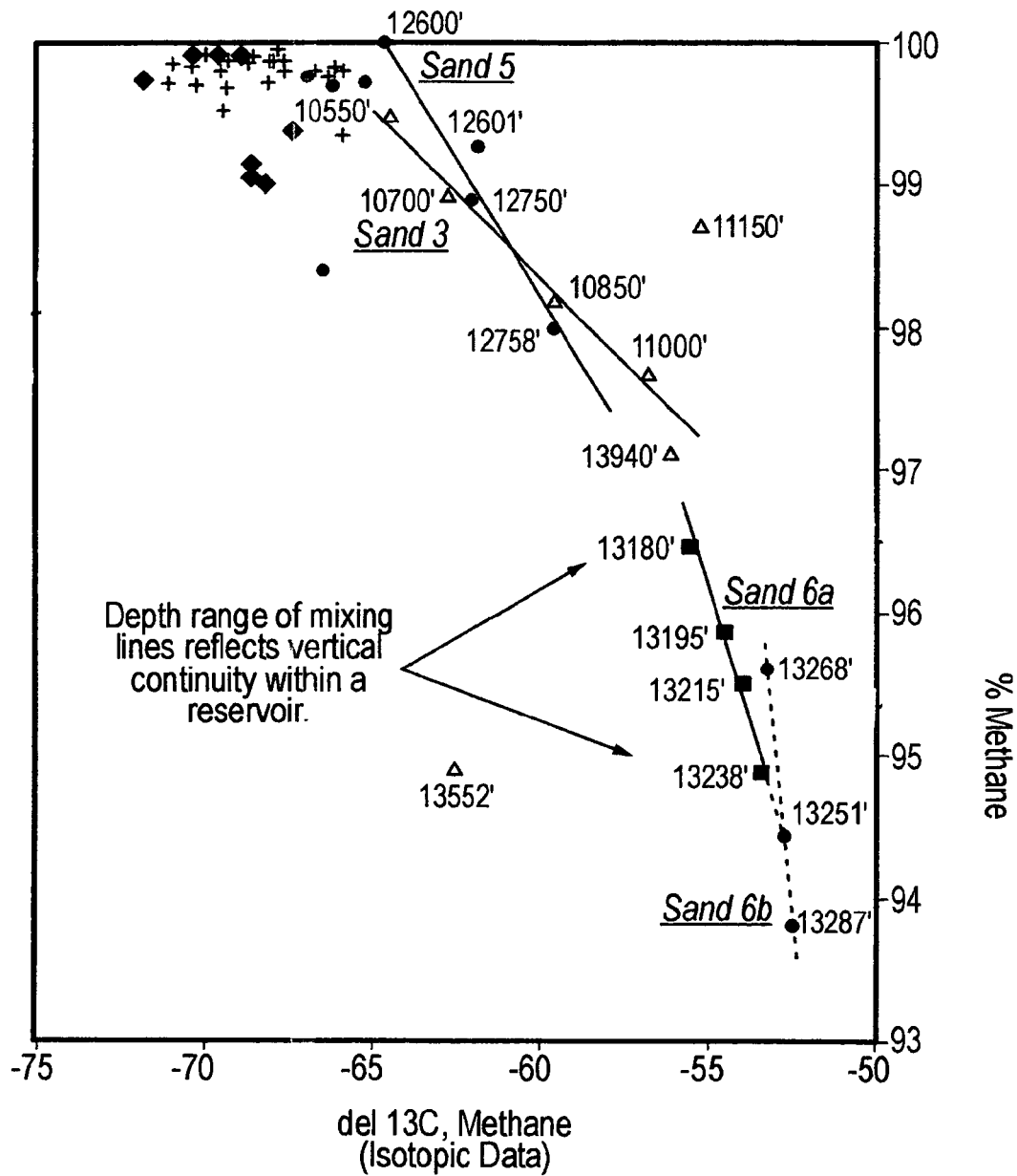
FIG. 8 illustrates a first exemplary gas mixing plot showing C1/Cn versus $\delta^{13}C_1$.
Figure 9:
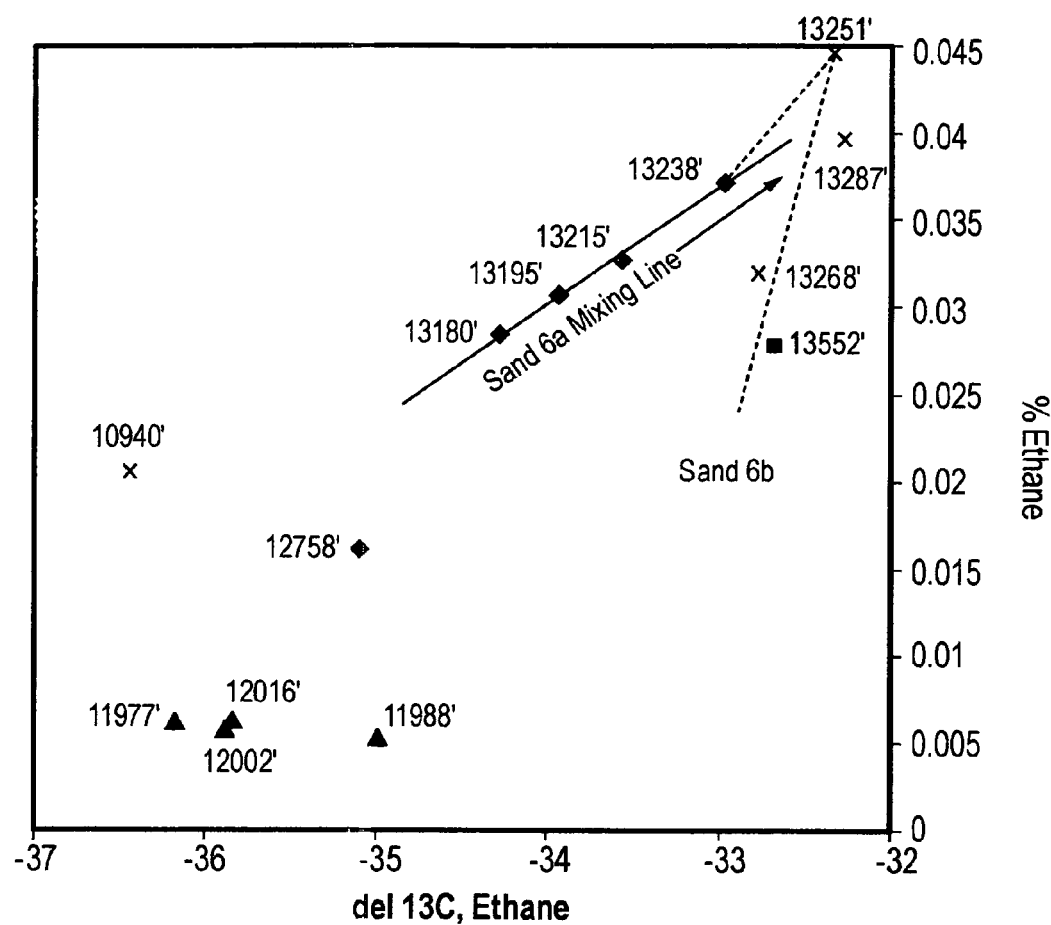
FIG. 9 illustrates a second exemplary gas mixing plot showing C2/Cn versus $\delta^{13}C_2$.

FIG. 7 illustrates an example drilling well log formed by percentage C1 to C6 hydrocarbons, gas units and isotopic data at various depths. FIG. 7 provides a real-world example of missed-pay, charge recognition, biodegradation and seal identification. An absence of gas shows also recognizes missed-pay potential due to operational drilling variables such as overbalanced mud weight. An absence of an isotopic show may be indicative of a non-economical background gas-charged sand or biodegraded gas/oil mixture. An isotopic peak profile may also recognize gas cap seal integrity in reservoirs. Gas shows correspond to isotopic shows in typical charged sands. Sand 6 illustrates thin shale in sand, which results in compartmentalization. FIGS. 8 and 9 show associated mixing lines.

FIG. 8 illustrates a gas mixing plot showing C1/Cn versus $\delta^{13}C_1$. Sands 3 and 5 (see FIG. 7) form closely approximating mixing lines, which indicate a possible relationship between these reservoirs. Sand 6a forms a good mixing line down to approximately 13251 feet, which while still within the reservoir suggests that this reservoir is compartmentalized. Separation of the mixing lines 6a and 6b illustrates identification of a seal, baffle or barrier between 13238 feet and 13251 feet. The depth range of mixing lines reflects vertical continuity within each reservoir.

FIG. 9 illustrates a gas mixing plot showing C2/Cn versus $\delta^{13}C_2$. This plot, similar to FIG. 8 employs ethane (C2) compositional and associated isotopic data to provide an early assessment of reservoir continuity and compartmentalization. Sand 6a represents a mixing line, whereas sand 6b is, at best, a different mixing line. Sand 6a mixing line terminates at a point between 13238 feet and 13251 feet (similar to FIG. 8) suggesting that a seal, baffle or barrier to communication may be present. Sand 6a and 6b appear to be separate compartments with zero or limited gas communication. The identification of a seal, baffle or barrier between 13238 feet and 13251 feet using ethane data further supports and validates similar interpretations arrived at in FIG. 8 using methane compositional and isotopic data.

Figure 10:
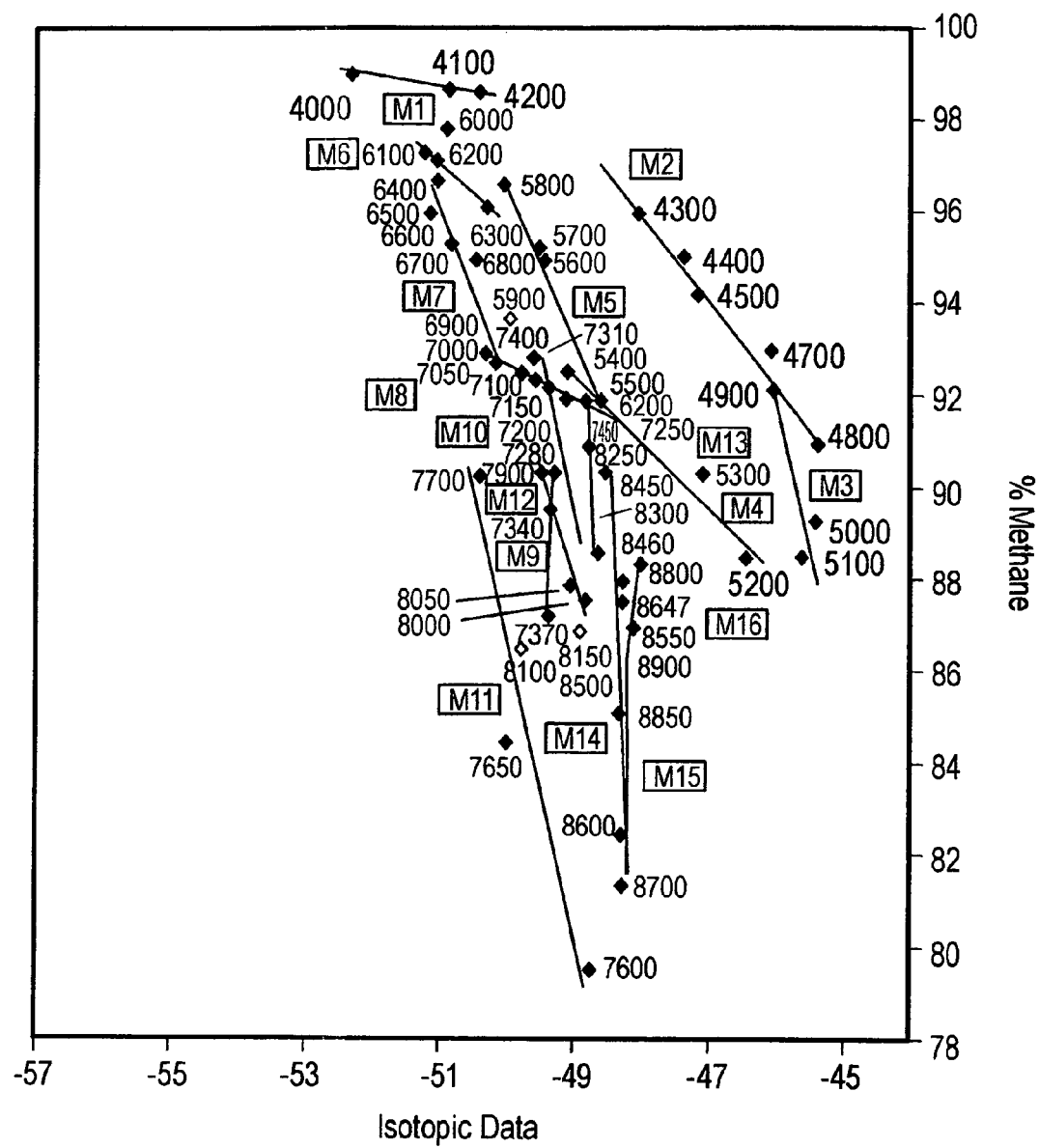
FIG. 10 illustrates a third exemplary gas mixing plot showing C1/Cn versus $\delta^{13}C_1$.

FIG. 10 illustrates another real-world example of a gas mixing plot showing C1/Cn versus $\delta^{13}C_1$ and shows an early assessment of reservoir continuity, compartmentalization and hydrocarbon communication. Mixing lines are easily recognized with the resulting depth range of lines reflecting separate compartments and continuity. The recognition of breaks (e.g. reference number 100) between related depth intervals (i.e., formation of separate mixing lines) suggests that a baffle or other lithological barrier to communication may exist. Mixing processes of sands and shales (e.g. reference number 200) in the circulating mud stream can also be observed.

Figure 11:
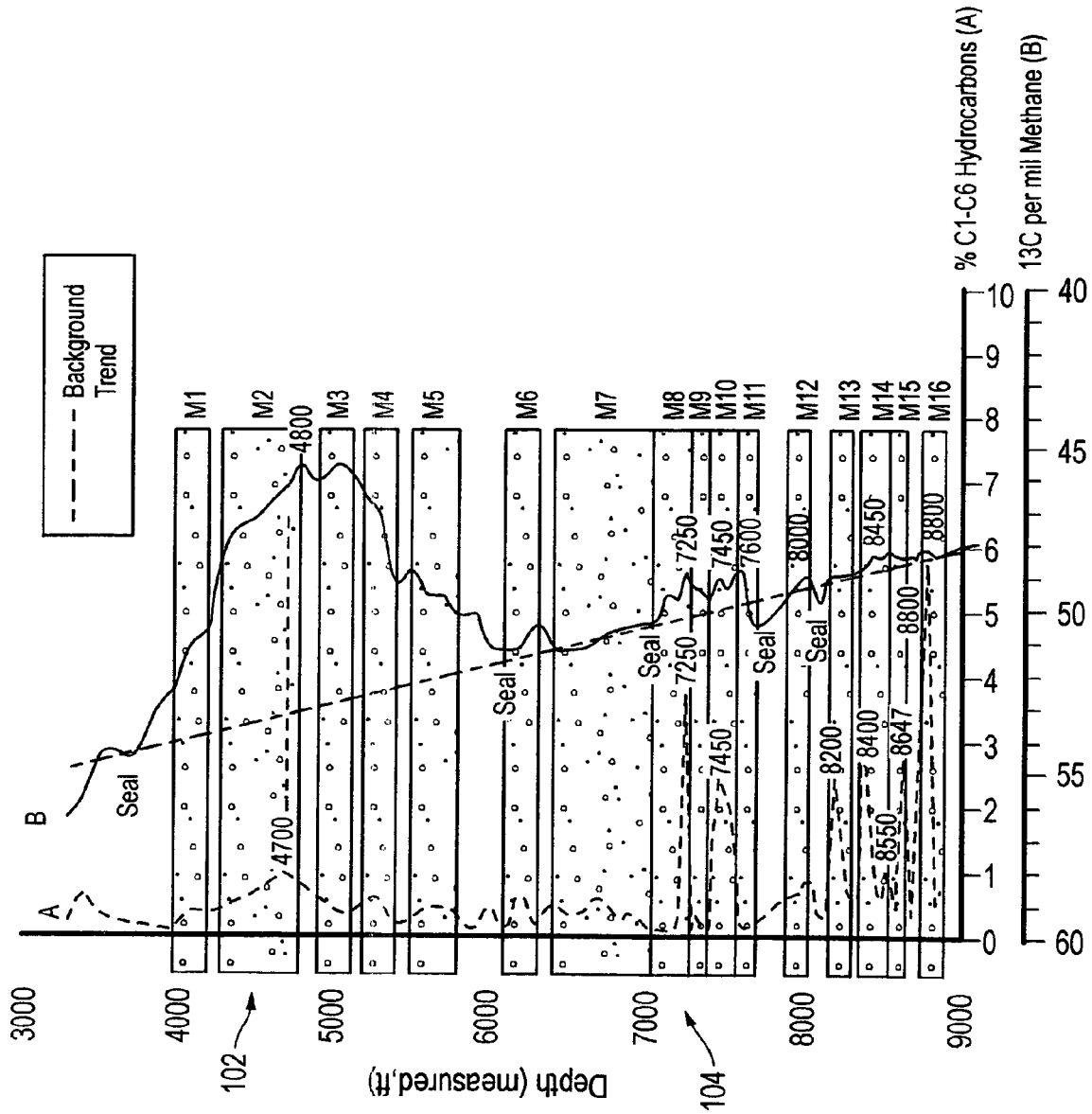
FIG. 11 illustrates an example well log formed by percentage C1–C6, gas units, and 13C methane.

FIG. 11 illustrates an example log percentage C1–C6 and 13C methane isotopic data. There are sixteen distinct gas communication compartments interpreted and identified.

Reference number 102 shows the mixing line depth ranges superimposed on the gas compositional and isotopic log depths. Reference number 104 shows where isotopic shows and the gas shows agree.

The present invention may be used for reservoir seal identification. Seal integrity measured as a function of its ability to restrict reservoir gas diffusion or other hydrocarbon leakage may be observed through mud gas isotope logging. Data from wells may indicate diffusion or leakage of reservoir gases into formations both above and below identified reservoirs. This data present and support potential identification of low- and high gas reservoir saturations. Low gas saturations are commonly ascribed to leaky seals. If there is a leaky seal, the gas in the overlying seal interval may develop an isotopic signal similar to that of the underlying reservoir gas, and in contrast to the background shale methane and ethane isotopic ratios. In contrast, an intact seal may have some mixing a short interval above the reservoir, but overall, the overlying lithology should have a lighter, more constant methane and ethane isotopic signal. Therefore, an intact seal as discussed above may indicate high gas saturation, combined with a distinctly different gas isotopic signature in the reservoir. Seals that are intact, and seals that leak, may be identifiable from a change in background isotopic signatures (See FIGS. 4 and 5). This provides calibration between physical property measurements of the shales or other caprocks and their ability to seal. Seals, however, may only be identified/recognized using this technique over a depth interval in which appropriate detailed mud gas isotope logging data have been acquired. This hydrocarbon diffusion or leakage process is likely to occur over geologic time and terminates upon contact with an impermeable barrier such as a continuous/homogeneous dense and compacted lithology (e.g. shale, marl, chalk, or other geological phenomena with associated pore pressure changes) of low porosity/permeability. Seals such as these may be generally referred to as 'trapping' seals, or more specifically as, 'regional' or 'localized' seals depending on their stratigraphic extent. These seals represent barriers to the potential migration of hydrocarbons. Identification of seals is important in establishing potential migration pathways and reservoir compartmentalization. Reservoir sands within identified particular regional seals are likely to contain gases of the same type and maturity.

Reservoir seals are not as well understood as either source or reservoir rocks, and evaluating and predicting reservoir seals remain problematic. Within this context, mud gas isotope logging is a promising technique for both complementing existing seal analysis methodology and empirically verifying the presence of any seal, regardless of origin.

Mud gas isotope logging is a noninvasive technique used to evaluate exploration and field production. Isotopic measurements made on mud gas samples from either side of a potentially sealing interval can be used to determine the effectiveness of a seal as well as establish likely migration pathways and reservoir compartmentalization. For example, in a thermogenic gas reservoir associated with a leaky seal, gas in the overlying seal may develop an isotopic signature similar to that of the underlying reservoir gas. This leaky seal isotopic signature will be isotopically heavier and contrast with methane and ethane isotopic ratios in background shales. In contrast, an effective seal in this same thermogenic setting will have an isotopically lighter and more constant methane and ethane signal. By measuring changes in background isotopic signal of intact seals vs.

seals that leak, calibration between physical property measurements of the seals and their ability to seal can be determined.

The present invention provides many advantages to existing interpretive techniques used in the oil and gas industry. The present invention provides an effective and accurate method of predicting or suggesting good hydrocarbon communication (compartments), barriers, and seals. The present invention uniquely interprets data through the use of mixing lines.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. A method of interpreting sampled mud gas compositional and isotopic data in a drilling operation of a target area, said method comprising the steps of:
   obtaining a plurality of mud gas samples from a target area;
   analyzing the plurality of mud gas samples to obtain hydrocarbon compositional and isotopic data from the samples;
   plotting the hydrocarbon compositional and isotopic data upon a chart or well log, wherein the step of of plotting the isotopic data upon a chart includes plotting a percentage methane versus isotopic composition;
   determining a trend of a plurality of points upon the chart;
   deriving from the chart or log an interpretation of the log indicative of hydrocarbon communication: and
   wherein the chart or log forms a mixing line derived from an approximately straight line or other trend comprised of at least three data points upon the plot, the indentified mixing line being indicative of a zone of good hydrocarbon communication and compartmentalization.

2. The method of interpreting sampled mud gas compositional and isotopic data of claim 1 wherein the isotopic composition includes determining a $\delta^{13}C$ and $^2H$ composition within the mud gas samples.

3. The method of interpreting sampled mud gas compositional and isotopic data of claim 1 wherein at least two mixing lines are derived from at least two straight lines.

4. The method of interpreting sampled mud gas compositional and isotopic data of claim 3 wherein a break between the two straight lines indicates a hydrocarbon communication barrier, baffle or seal.

5. The method of interpreting sampled mud gas compositional and isotopic data of claim 4 wherein the break is large and is indicative of a seal.

6. The method of interpreting sampled mud gas compositional and isotopic data of claim 4 wherein the break is small and is indicative of a baffle or other barrier to hydrocarbon communication.

7. The method of interpreting sampled mud gas compositional and isotopic data of claim 1 wherein:
   at least a first mixing line and a second mixing line are derived, the first mixing line being adjacent the second mixing line; and
   the second mixing line reverses direction from the first mixing line indicating a compartment or reservoir.

8. The method of interpreting sampled mud gas compositional and isotopic data of claim 1 wherein;
   At least a first mixing line and a second mixing line are derived, the first mixing line being adjacent the second mixing line; and
   the second mixing line being substantially deviated from the first mixing line, thereby indicating a lithological seal, baffle or barrier.

9. A method of interpreting sampled mud gas compositional and isotopic data from a target area and plotted on a chart, said method comprising the steps of:
   determining mixing lines from the chart, the mixing lines being at least three data points plotting on the chart that approximate a substantially straight line or other trend; and
   analyzing the mixing lines to determine hydrocarbon communication within the target area;
   wherein the chart includes a percentage methane versus isotopic composition for the sampled mud gas data.

10. The method of interpreting sampled mud gas data from claim 9 wherein each mixing line indicates good hydrocarbon communication.

11. The method of interpreting sampled mud gas data from claim 9 wherein the step of analyzing the mixing lines includes determining a break between two mixing lines that indicate a barrier, baffle or seal in the hydrocarbon communication.

12. The method of interpreting sampled mud gas data from claim 9 wherein the isotopic composition includes determining a $\delta^{13}C$ and $^2H$ composition within the mud gas samples.

13. The method of interpreting sampled mud gas data from claim 9 wherein the step of analyzing the mixing lines includes determining an indication of a hydrocarbon seal.

14. The method of interpreting sampled mud gas compositional and isotopic data of claim 13 wherein two mixing lines form a large break indicative of the hydrocarbon seal.

15. The method of interpreting sampled mud gas compositional and isotopic data of claim 13 wherein two mixing lines form a small break indicative of a baffle or other barrier to hydrocarbon communication.

16. The method of interpreting sampled mud gas compositional and isotopic data of claim 9 wherein:
   at least a first mixing line and a second mixing line are determined, the first mixing line being adjacent the second mixing line; and
   the second mixing line reverses direction from the first mixing line to indicate a compartment or reservoir.

17. The method of interpreting sampled mud gas compositional and isotopic data of claim 9 wherein:
   at least a first mixing line and a second mixing line are determined, the first mixing line being adjacent the second mixing line; and
   the second mixing line being substantially deviated from the first mixing line to indicate a lithological seal, baffle or barrier.

18. A method of interpreting sampled mud gas compositional and isotopic data from a target area in a drilling operation, said method comprising the steps of:

plotting the compositional and isotopic data upon a chart, the chart illustrating a percentage methane versus isotopic composition for the sampled mud gas data;

determining mixing lines from the chart, the mixing lines being at least three data points approximating a substantially straight line or other trend; and analyzing the mixing lines to determine hydrocarbon communication within the target area.

19. The method of interpreting sampled mud gas compositional and isotopic data of claim 18, wherein the isotopic composition includes a $\delta^{13}C$ and $^2H$ composition within the mud gas samples.

20. The method of interpreting sampled mud gas compositional and isotopic data of claim 18 wherein the step of analyzing the mixing lines includes determining a break between two mixing lines.

21. The method of interpreting sampled mud gas compositional and isotopic data of claim 20 wherein the break is indicative of a hydrocarbon barrier, baffle or seal.

* * * * *